United States Patent
Botich et al.

(10) Patent No.: US 7,300,416 B2
(45) Date of Patent: *Nov. 27, 2007

(54) PRE-FILLED RETRACTABLE NEEDLE INJECTION AMPOULES

(75) Inventors: Michael J. Botich, Reno, NV (US); Thor R. Halseth, Agoura, CA (US)

(73) Assignee: Specialized Health Products International, Bountiful, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/724,663

(22) Filed: Dec. 1, 2003

(65) Prior Publication Data

US 2004/0111063 A1 Jun. 10, 2004

Related U.S. Application Data

(63) Continuation of application No. 09/670,182, filed on Sep. 26, 2000, now abandoned, which is a continuation-in-part of application No. 08/922,905, filed on Sep. 3, 1997, now Pat. No. 6,123,688, which is a continuation-in-part of application No. 08/699,998, filed on Aug. 20, 1996, now Pat. No. 5,788,677.

(60) Provisional application No. 60/050,797, filed on Jun. 26, 1997, provisional application No. 60/025,342, filed on Sep. 3, 1996, provisional application No. 60/005,895, filed on Oct. 26, 1995, provisional application No. 60/004,450, filed on Sep. 29, 1995, provisional application No. 60/002,630, filed on Aug. 22, 1995.

(51) Int. Cl.
*A61M 5/32* (2006.01)
*A61M 5/00* (2006.01)

(52) U.S. Cl. ...................... 604/110; 604/195

(58) Field of Classification Search ........... 604/195, 604/187, 200, 201, 203, 205, 231, 232, 244, 604/91, 110, 196, 263, 192, 218; 128/919

See application file for complete search history.

(56) References Cited

U.S. PATENT DOCUMENTS

| | | |
|---|---|---|
| 2,408,323 A | 8/1946 | Lockhart |
| 2,453,591 A | 11/1948 | Poux |
| 2,551,339 A | 5/1951 | Ryan et al. |
| 2,562,129 A | 7/1951 | Scherer et al. |
| 2,671,449 A | 3/1954 | Dann |

(Continued)

*Primary Examiner*—Matthew DeSanto
(74) *Attorney, Agent, or Firm*—Paul S. Evans; Kevin Laurence

(57) ABSTRACT

Pre-filled injection ampoules for administering a readily-available dose of fluid medication, are provided with a retractable needle. The needle is held in a projecting configuration from a barrel against a rearward bias exerted on the needle by a spring located within a spring housing. A piston is positioned within the barrel for expelling the fluid medication therefrom. The piston is configured to release the needle after completion of an injection stroke and to receive the needle in an internal cavity. In alternative embodiments, a retractable-needle injection device includes a housing for receiving a pre-filled medication cartridge of the type having a slidable piston positioned therein. A stationary plunger is located within the housing for maintaining the piston at a fixed location as the cartridge is urged into the housing to administer an injection. After the end of an injection stroke, the cartridge is further urged into the housing to release a effectuate retraction.

17 Claims, 12 Drawing Sheets

U.S. PATENT DOCUMENTS

| | | |
|---|---|---|
| 2,671,450 A | 3/1954 | Dann |
| 2,708,438 A | 5/1955 | Cohen |
| 2,778,360 A | 1/1957 | Miskel |
| 2,841,143 A | 7/1958 | Bertram |
| 2,876,770 A | 3/1959 | White |
| 3,306,290 A | 2/1967 | Weltman |
| 3,401,693 A | 9/1968 | Cohen |
| 3,739,780 A | 6/1973 | Ogle |
| 3,766,919 A | 10/1973 | Cloyd |
| 3,820,652 A | 6/1974 | Thackston |
| 3,825,003 A | 7/1974 | Kruck |
| 3,870,044 A | 3/1975 | Burke et al. |
| 3,916,894 A | 11/1975 | Cloyd |
| 3,941,131 A | 3/1976 | Ogle |
| 3,989,044 A | 11/1976 | Meierhoefer |
| 4,009,716 A | 3/1977 | Cohen |
| 4,078,565 A | 3/1978 | Genese |
| 4,445,895 A | 5/1984 | Margulies |
| 4,507,117 A | 3/1985 | Vining et al. |
| 4,747,829 A | 5/1988 | Jacob et al. |
| 4,767,413 A | 8/1988 | Haber et al. |
| 4,778,453 A | 10/1988 | Lopez |
| 4,790,827 A | 12/1988 | Haber et al. |
| 4,808,169 A | 2/1989 | Haber et al. |
| 4,820,275 A | 4/1989 | Haber et al. |
| 4,826,489 A | 5/1989 | Haber et al. |
| 4,834,717 A | 5/1989 | Haber et al. |
| 4,838,863 A | 6/1989 | Allard et al. |
| 4,838,869 A | 6/1989 | Allard |
| 4,874,382 A | 10/1989 | Lindemann et al. |
| 4,892,523 A | 1/1990 | Haber et al. |
| 4,900,307 A | 2/1990 | Kulli |
| 4,904,242 A | 2/1990 | Kulli |
| 4,906,236 A | 3/1990 | Alberts et al. |
| 4,909,794 A | 3/1990 | Haber et al. |
| 4,915,702 A | 4/1990 | Haber |
| 4,917,673 A | 4/1990 | Coplin |
| 4,919,657 A | 4/1990 | Haber et al. |
| 4,927,414 A | 5/1990 | Kulli |
| 4,931,040 A | 6/1990 | Haber et al. |
| 4,936,830 A | 6/1990 | Verlier |
| 4,947,863 A | 8/1990 | Haber et al. |
| 4,966,593 A | 10/1990 | Lennox |
| 4,994,034 A | 2/1991 | Botich et al. |
| RE33,585 E | 5/1991 | Haber et al. |
| 5,019,052 A | 5/1991 | Rohrbough |
| 5,049,133 A | 9/1991 | Villen |
| 5,053,010 A | 10/1991 | McGary et al. |
| 5,067,490 A | 11/1991 | Haber |
| 5,090,962 A | 2/1992 | Landry, Jr. et al. |
| 5,098,382 A | 3/1992 | Haber et al. |
| 5,098,403 A | 3/1992 | Sampson |
| 5,112,307 A | 5/1992 | Haber et al. |
| 5,114,404 A | 5/1992 | Paxton et al. |
| 5,129,884 A | 7/1992 | Dysarz |
| RE34,045 E | 8/1992 | McFarland |
| 5,167,641 A | 12/1992 | Schmitz |
| 5,169,392 A | 12/1992 | Randford et al. |
| 5,180,369 A | 1/1993 | Dysarz |
| 5,188,599 A | 2/1993 | Botich et al. |
| 5,193,552 A | 3/1993 | Columbus et al. |
| 5,201,708 A | 4/1993 | Martin |
| 5,207,647 A | 5/1993 | Phelps |
| 5,219,333 A | 6/1993 | Sagstetter et al. |
| 5,232,456 A | 8/1993 | Gonzalez |
| 5,246,428 A | 9/1993 | Falknor |
| 5,261,880 A | 11/1993 | Streck et al. |
| 5,263,942 A | 11/1993 | Smedley et al. |
| 5,267,976 A | 12/1993 | Guerineau et al. |
| 5,269,760 A | 12/1993 | Bina |
| 5,290,256 A | 3/1994 | Weatherford et al. |
| 5,295,963 A | 3/1994 | Deeks |
| 5,308,332 A | 5/1994 | Dillard, III et al. |
| 5,322,515 A | 6/1994 | Karas et al. |
| 5,330,430 A | 7/1994 | Sullivan |
| 5,338,311 A | 8/1994 | Mahurkar |
| 5,342,310 A | 8/1994 | Ueyama et al. |
| 5,350,367 A | 9/1994 | Stiehl et al. |
| 5,358,491 A | 10/1994 | Johnson et al. |
| 5,360,408 A | 11/1994 | Vaillancourt |
| 5,385,551 A | 1/1995 | Shaw |
| 5,389,085 A | 2/1995 | D'Alessio et al. |
| 5,399,170 A | 3/1995 | Whitley |
| 5,401,246 A | 3/1995 | Mazur et al. |
| 5,403,287 A | 4/1995 | Talonn et al. |
| 5,407,431 A | 4/1995 | Botich et al. |
| 5,407,436 A | 4/1995 | Toft et al. |
| 5,417,660 A | 5/1995 | Martin |
| 5,423,758 A * | 6/1995 | Shaw ........................ 604/110 |
| 5,458,580 A | 10/1995 | Hajishorch |
| 5,478,324 A | 12/1995 | Meyer |
| 5,487,732 A * | 1/1996 | Jeffrey ........................ 604/110 |
| 5,501,670 A | 3/1996 | Sak |
| 5,520,642 A | 5/1996 | Bigagli et al. |
| 5,527,285 A | 6/1996 | Lenz et al. |
| 5,531,694 A | 7/1996 | Clemens et al. |
| 5,531,706 A | 7/1996 | de la Fuente |
| 5,538,507 A | 7/1996 | De Kler et al. |
| 5,549,572 A | 8/1996 | Byrne et al. |
| 5,573,512 A | 11/1996 | van den Haak |
| 5,575,777 A | 11/1996 | Cover et al. |
| 5,593,391 A | 1/1997 | Stanners |
| 5,601,535 A | 2/1997 | Byrne et al. |
| 5,632,733 A | 5/1997 | Shaw |
| 5,634,903 A | 6/1997 | Kurose et al. |
| 5,685,863 A | 11/1997 | Botich et al. |
| 5,695,475 A | 12/1997 | Best, Jr. et al. |
| 5,709,669 A | 1/1998 | Haining |
| 5,788,677 A | 8/1998 | Botich et al. |
| 5,800,395 A | 9/1998 | Botich et al. |
| 5,891,105 A | 4/1999 | Mahurkar |
| 5,957,897 A | 9/1999 | Jeffrey |
| 5,997,512 A | 12/1999 | Shaw |
| 6,004,278 A | 12/1999 | Botich et al. |
| 6,010,486 A | 1/2000 | Carter et al. |
| 6,015,438 A | 1/2000 | Shaw |
| 6,569,115 B1 * | 5/2003 | Barker et al. ............... 604/110 |

* cited by examiner

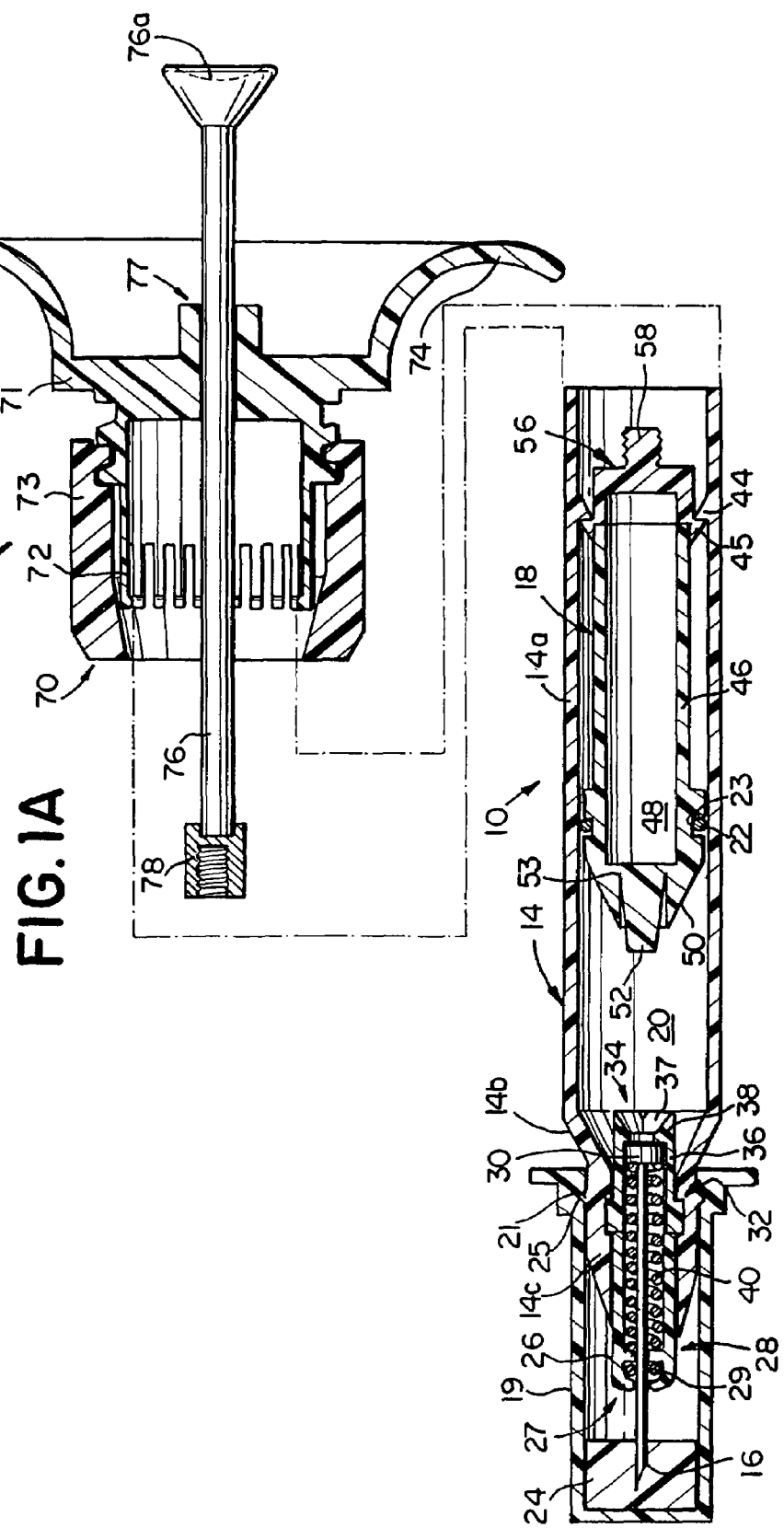

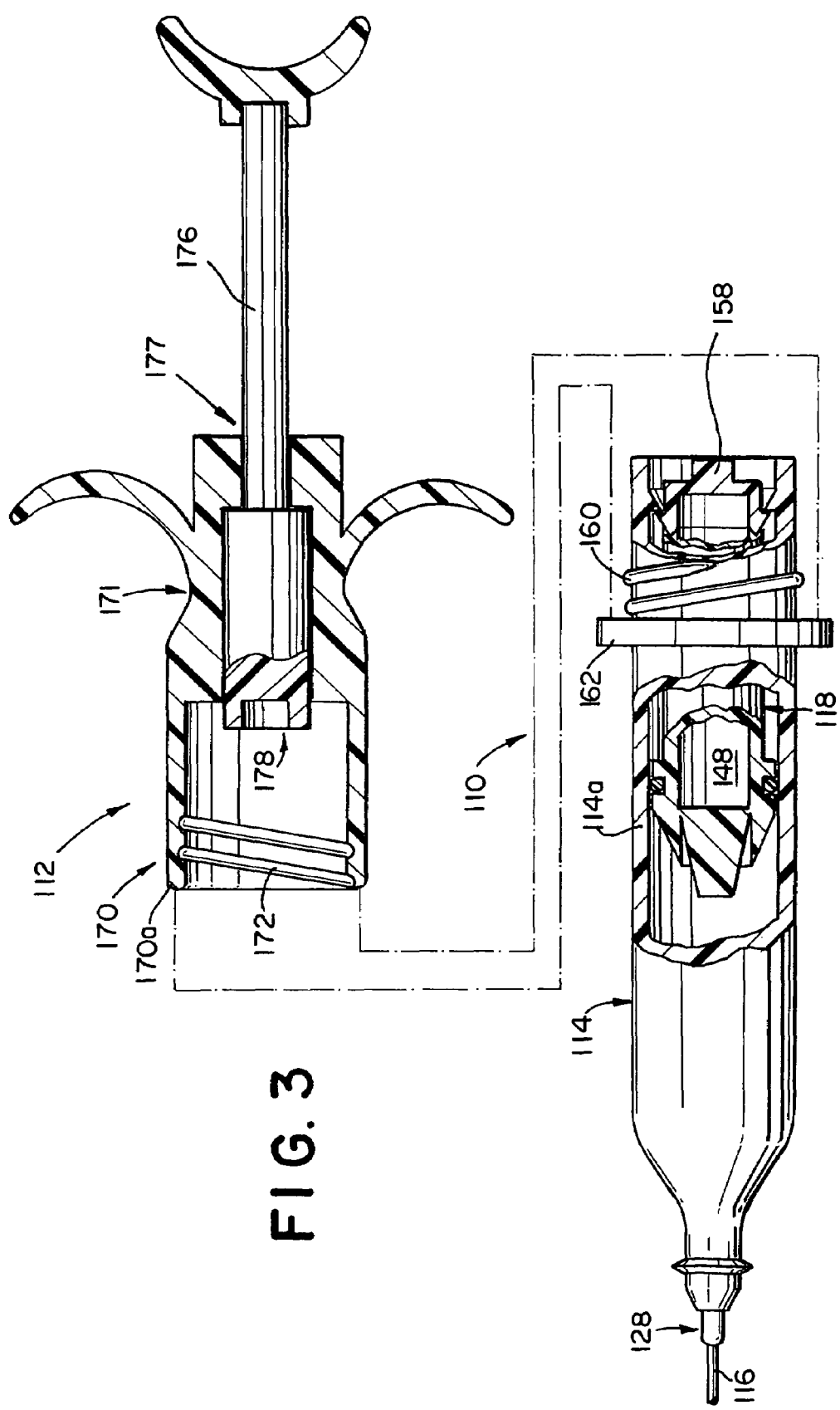

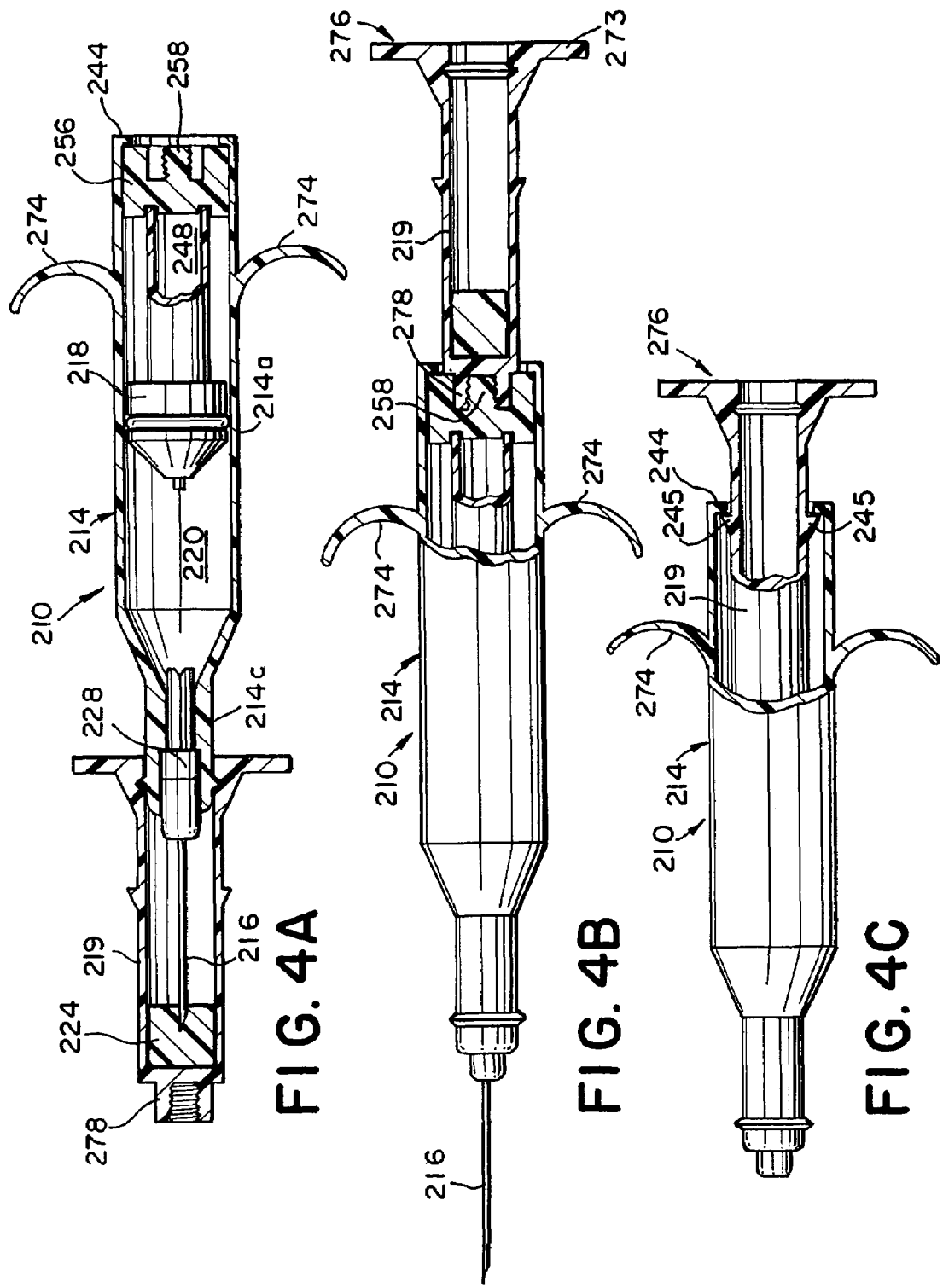

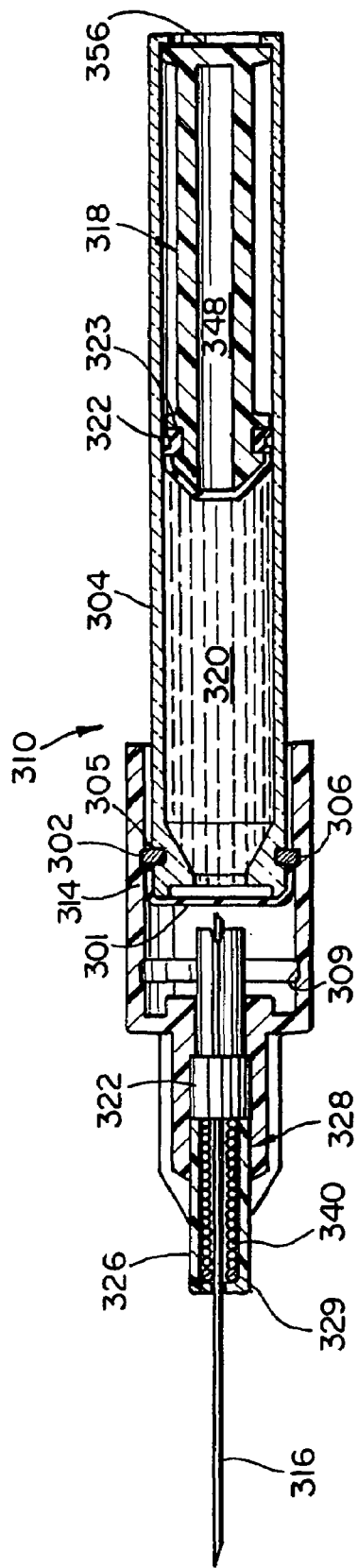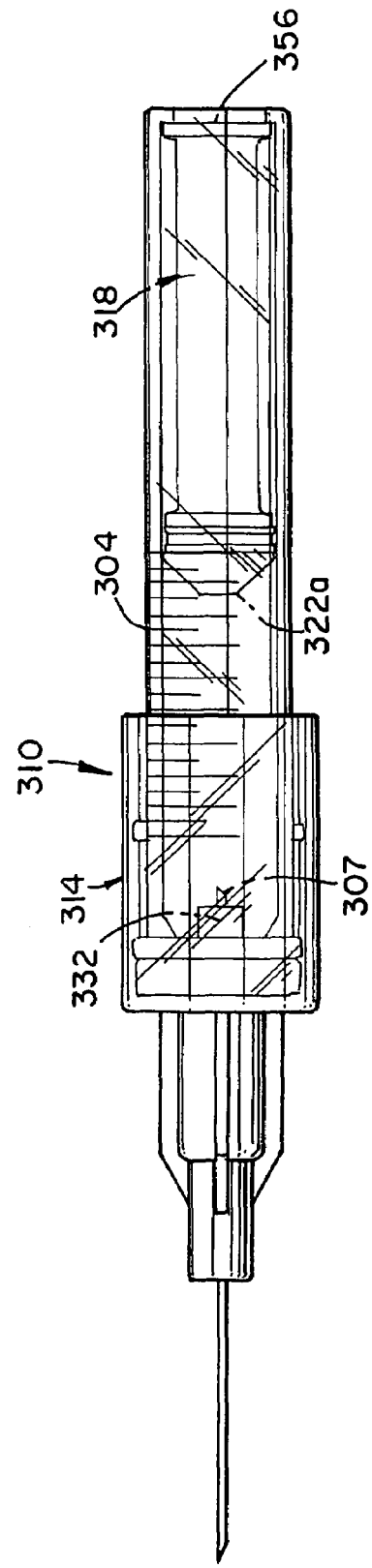

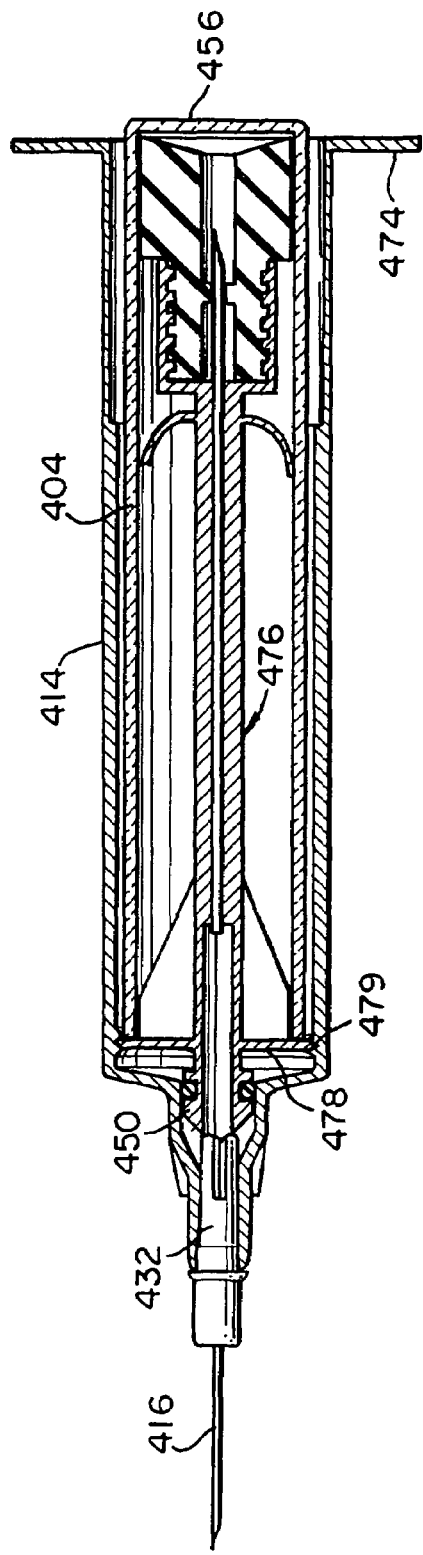
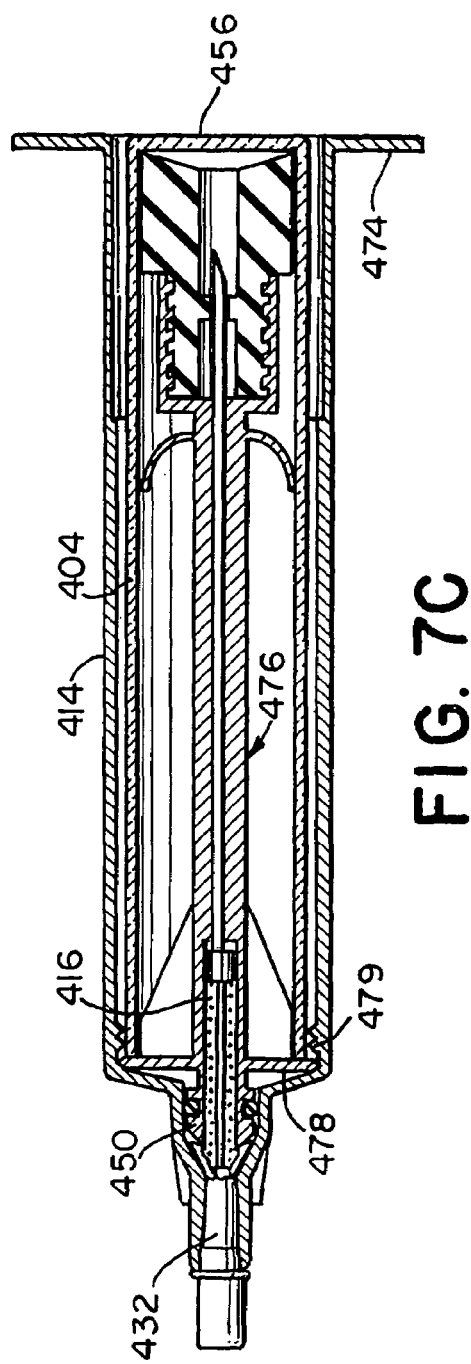

PRE-FILLED RETRACTABLE NEEDLE INJECTION AMPOULES

CROSS-REFERENCED TO RELATED APPLICATIONS

This application is a continuation of application Ser. No. 09/670,182, filed Sep. 26, 2000, which is a continuation-in-part of U.S. patent application Ser. No. 08/922,905, filed Sep. 3, 1997, which issued on Sep. 26, 2000 as U.S. Pat. No. 6,123,688, which is a continuation-in-part of U.S. patent application Ser. No. 08/699,998, filed Aug. 20, 1996, which issued on Aug. 4, 1998 as U.S. Pat. No. 5,788,677, in which priority is claimed to each of U.S. Provisional Application No. 60/002,630, filed Aug. 22, 1995; U.S. Provisional Application No. 60/004,450, filed Sep. 29, 1995; and Provisional Application No. 60/005,895, filed Oct. 26, 1995. Priority under 35 U.S.C. .sctn. 119(e) is also claimed herein to U.S. Provisional Application No. 60/025,342, filed Sep. 3, 1996 and U.S. Provisional Application No. 60/050,797, filed Jun. 26, 1997.

Each of the aforementioned applications is hereby incorporated herein by reference.

FIELD OF THE INVENTION

The present invention relates to pre-filled ampoules, carpules, or cartridges for administering injections of medicinal fluids to patients. More specifically, the invention relates to such devices having a retractable needle feature for rendering them non-reusable and safely disposable.

BACKGROUND OF THE INVENTION

Since the late 1980s, a variety of retractable needle injection syringes have been developed to decrease the risk of needle stick injuries after intravenous or intramuscular administration of fluid medication. Such syringes may be broadly categorized as having a manually retractable needle or an automatically retractable needle. In manually retractable needle syringes, the piston of the syringe is adapted to engage the needle or the needle hub and to permit the needle or hub to be withdrawn into the barrel of the syringe when the piston is pulled rearwardly after an injection stroke. Such syringes are exemplified by U.S. Pat. No. 4,507,117 to Vining et al.; U.S. Pat. No. 4,692,156 to Haller; and U.S. Pat. No. 4,710,170 and numerous later variations thereof, to Haber et al.

In automatically retractable needle syringes, a spring-loaded retraction mechanism is provided for driving the needle into an interior compartment upon actuation of a latch associated with the retraction mechanism. Such syringes are shown and described in U.S. Pat. No. 4,994,034 to Botich and Halseth.

Prior to retracting the needle, the aforementioned retractable needle syringes are used in substantially the traditional manner, e.g., by initially drawing fluid medication into the syringe by inserting the needle into a supply of medication, and then withdrawing the piston in order to draw the medication into the barrel of the syringe. Then, the dosage of the medication is adjusted, and air bubbles removed from the barrel, by ejecting a portion of the withdrawn medication from the syringe while holding the syringe in an upright position. The traditional practice for preparing an injection can be wasteful, hazardous, and can lead to dosage errors. Moreover, in an emergency situation, precious moments can be lost while an injection is prepared. To circumvent these problems, several types of pre-filled injection systems, such as Sterling Winthrop's "CARPUJECT", Wyeth-Ayerst Laboratories' "TUBEX" and Abbot Laboratories' "ABBOJECT" injection systems, have become popular alternatives to the traditional vial-and-syringe method of storing and administering injectable medications.

It would be desirable to provide the advantages of automatic needle retraction for pre-filled fluid medication injection systems and to further improve such pre-filled injection systems for reduced manufacturing costs and enhanced ease of use. Because of the substantial market penetration and professional acceptance of the aforementioned commercially-available injection systems, it would also be desirable to provide automatic retraction capability for pre-filled injection ampoules.

SUMMARY OF THE INVENTION

In accordance with the present invention, there is provided an injection device operable with a pre-filled medication ampoule or cartridge. The injection device has an automatic needle retraction capability so that after the medicinal fluid is injected into the patient, the needle is automatically retracted to prevent inadvertent contact with the contaminated needle.

The injection device includes a hollow housing and a needle operable between a projecting position in which the sharpened tip projects forwardly from the housing and a retracted position in which the sharpened tip is shielded against inadvertent contact. A biasing element biases the needle toward the retracted position. A stem disposed within the housing is configured to matingly engage the ampoule to attach the ampoule to the device. A latch releasably retains the stem at a fixed axial position during injection. The latch is configured to cooperate with the rim of the ampoule so that at the end of the injection stroke the ampoule engages the latch. After the ampoule engages the latch, continued forward displacement of the ampoule operates to retract the needle.

In accordance with another aspect, the present invention also provides a medical device having a needle retainer that releasably retains the needle in the projecting position during use. The needle retainer is formed of a radially deformable arm. The needle is retracted after use by displacing the ampoule forwardly. More specifically, displacing the ampoule forwardly operates to affect retraction by displacing the arm radially outwardly. The biasing element then displaces the needle rearwardly so that the sharpened tip is protected against inadvertent contact.

In accordance with yet another aspect, the present invention also provides a device having a plunger disposed within a hollow housing. A stem attached to the plunger is configured to matingly engage the ampoule to attach the ampoule to the device. A radially deformable arm extends radially from the plunger into engagement with a recess in the housing to impede relative displacement in a first direction between the plunger and the housing. The arm is configured so that upon forward displacement of the ampoule, the rim of the ampoule engages the arm, deforming the arm radially inwardly so that the arm disengages the recess in the housing. Retraction is actuated after use by displacing the ampoule forwardly. The biasing element then displaces the needle into the retracted position.

BRIEF DESCRIPTION OF THE DRAWINGS

The foregoing summary, as well as the following detailed description, will be best understood in conjunction with the attached drawings in which:

FIG. 1A is a cross-sectional view of a retractable needle injection ampoule and an injector assembly therefor, according to a first embodiment of the invention;

FIG. 3 is a cross-sectional view of a retractable needle injection ampoule and an injector assembly according to a second embodiment of the invention;

FIGS. 4A-4C are partial sectional views of a self-contained retractable needle injection ampoule and injector, in respective configurations prior to, during, and after use thereof;

FIG. 5A is a partial sectional view of a fourth embodiment of a retractable needle injection ampoule in an initial configuration;

FIG. 5B is perspective view of the injection ampoule of FIG. 5A, in a prepared configuration;

FIGS. 7A-7C are partial sectional views of a fifth embodiment of a retractable needle injection ampoule, in respective configurations prior to, during, and after use thereof;

DETAILED DESCRIPTION

Figure 1B:
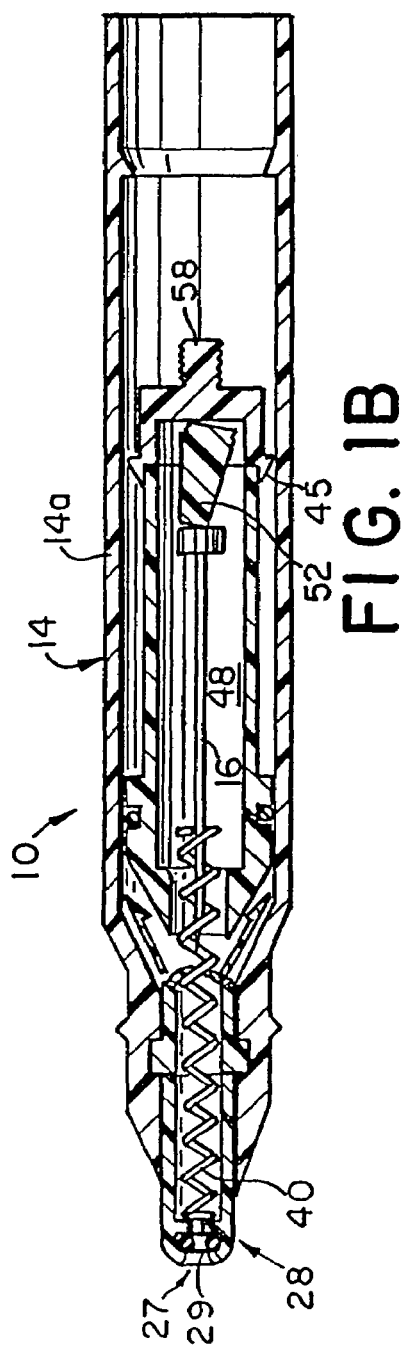
FIG. 1B is a cross-sectional view of the ampoule of FIG. 1A with the needle in the retracted position.

Referring now to FIG. 1A, there is shown a retractable needle injection ampoule 10 and an attachable injector assembly 12. The ampoule 10 has a main body or housing 14, which comprises a tubular barrel 14a, a reduced diameter tubular forward portion 14c, and a frustoconical portion 14b disposed between the barrel 14a and the forward portion 14c. The rear end of the barrel 14a is open to receive a piston 18 therein during assembly of the ampoule. The interior of the barrel 14a defines a chamber 20 containing a volume of medicinal fluid, preferably in an amount sufficient for a single dose of the fluid or in an amount preferred for administration to a single patient, is contained within the remaining forward portion of the barrel 14a in front of the piston 18. A sealing member 22 is engaged within a seat 23 formed in the forward end of the piston 18. The sealing member 22 is slidably engaged with the interior of the barrel 14a forming a seal to prevent the fluid from leaking out of the chamber 20 through the rear of the barrel 14a.

The barrel 14 is preferably formed of a material that is chemically compatible with the fluid medication to be stored in the chamber 20. For storage of some medications, polypropylene is a suitable inert material. For storage of other medications, glass may be preferred for forming the barrel 14.

A tubular needle 16 extends from the forward end of the ampoule 10. The needle is preferably made of stainless steel for chemical compatibility with various medications. The rear or back end of the needle 16 includes an enlarged head 30 positioned thereon. In the configuration shown in FIG. 1A, the rear portion of the needle 16 extends generally axially within a spring housing assembly 28. The spring housing assembly 28 is held within the forward portion 14c of the main housing 14. A spring 40 surrounds the needle 16 within the spring housing assembly. The spring housing assembly 28 includes a front alignment portion 26 and a rear needle retaining portion 32. The front alignment portion 26 has an needle guideway 27 formed in the forward portion thereof, through which the needle 16 extends in the projecting configuration. The needle guideway 27 is sized for maintaining the needle 16 in axial alignment. A sealing member 29, such as a resilient washer, silicone plug, or puncturable disc, is disposed within an interior circumferential channel formed within the forward portion of the front alignment portion 26. The sealing member 29 surrounds the needle 16. The sealing member 26 further promotes axial alignment of the needle 16, and also serves to prevent fluid from passing through the needle guideway 27 subsequent to retraction of the needle 16.

The front alignment member 26 is firmly engaged within the forward portion 14c of the main housing 14, e.g. by friction. The engagement of the alignment member 26 within the forward portion 14c of the housing 14 may be further secured by epoxy or ultrasonic welding. Other effective means for securing the alignment member 26 within the forward portion 14c of the housing 14 include cooperative bayonet projections and grooves (not shown) formed upon the alignment member 26 and within the forward portion 14c, locking screw threads, or equivalent structures for providing for secure assembly of the respective components.

The tubular needle retaining portion 32 is positioned to form the rear of the spring housing assembly 28. The forward end of the needle retaining member 32 abuts against the rearward end of the front alignment member 26. The rear end of the needle retaining member 32 is provided with a latch mechanism generally designated 34.

A tubular removable sheath or cap 19 is removably mounted on the exterior of the forward portion 14c of the housing 14. The cap 19 is held upon the forward portion 14c of the housing by, for example, cooperative engagement between a lateral protrusion 21 formed upon the exterior of the forward portion 14c of the housing 14 and an annular mating recess 25 formed within the rear of the cap 19. The cap 19 surrounds and shields the needle 16 prior to use of the ampoule 10. The tip of the needle 16 is positioned or embedded within a plug member 24. The plug member 24 seals the forward end of the needle 16 in order to prevent the fluid 20 from leaking out of the tip of the needle 16 prior to use of the ampoule. The plug member 24 is preferably engaged with the interior of the cap 19, so that when the cap 19 is removed from the housing 14 to expose the needle immediately prior to administering an injection, the plug member 24 is likewise removed from the tip of the needle 16.

The plug member 24 may be formed within the cap 19 during assembly thereof by depositing a quantity of a silicone elastomer, or other material suitable for subsequent penetration by the needle 16, within the forward interior of the cap 19. The material employed to form the plug should be selected for biological and chemical compatibility with the medicinal fluid, to avoid contamination of the fluid, allergic reactions, or other undesirable effects. After the elastomer has cured, the cap 19 is urged onto the forward portion 14c of the housing 14. As the cap 19 is positioned upon the housing 14, the needle penetrates the plug member 24 to be sealed thereby.

The rear end of the barrel 14a is open to receive a piston 18 therein. The piston 18 includes a shaft 46 positioned axially within the barrel 14a and having an axial channel or cavity 48 formed therein. An annular groove 23 is formed about the forward end of the piston 18 for retaining a sealing member or O-ring 22. The cavity 48 is appropriately sized to receive the needle 16 therein when the needle 16 is retracted. The rear end of the axial cavity is closed by an end member or piston cap 56. The piston cap 56 abuts against, or is joined to, the rear of the piston shaft 46. An engaging member, such as a boss 58, is formed on the cap 56 and extends from the rear surface of the piston 18.

The piston 18 and the barrel 14a include cooperating means for positioning and retaining the piston toward the rear of the barrel 14a and for preventing rearward motion of the piston 18 out of the rear of the barrel 14a. For example, an annular detent 44 may be formed circumferentially about the interior of the barrel 14a for engaging one or more tabs 45 projecting radially from the exterior of the piston 18. The detent 44 preferably has an obliquely angled rear surface and a more nearly perpendicular forward surface. The tabs 45 have complementary angled surfaces to permit the piston to be inserted into the barrel 14a and positioned as shown in FIG. 1A during assembly of the ampoule 10. A removable rear cap (not shown) may also be provided to cover the rear of the barrel 14a prior to use, in order to prevent the rear of the piston 18 from being accidentally or inadvertently pushed upon during transportation, storage, or other handling of the ampoule 10.

The medicinal fluid contained within chamber 20 and stored within the ampoule 10 prior to use, may be charged during assembly of the ampoule 10 as follows. The main housing 14 is initially provided with neither the piston 18 nor the spring housing assembly 28 installed therein. First, the piston 18 is inserted into the rear of the barrel 14a and is urged into engagement with the detent 44. Then, holding the main housing 14 upright, the volume of fluid 20 may be dispensed from a suitable dispenser into the ampoule 10 through the axial cavity within the forward portion 14c of the housing. The spring housing assembly 28, and the associated needle 16 may then be installed in the forward portion 14c of the housing. The spring housing assembly 28 may be installed by first inserting the needle retaining portion 32 into the forward portion 14c, positioning the needle 16 and the surrounding spring 40 within the needle retaining portion 32, and then sliding the front alignment portion 26 of the spring housing assembly 28 onto the needle and into engagement with the forward portion 14c of the main housing 14 in accordance with the aforementioned engagement means therebetween. The small volume of air remaining within the needle may be purged by the user prior to administering an injection, as is customary in administering injections.

In an alternative assembly procedure, the front alignment portion 26 and the needle retaining portion 32 of the spring housing assembly 28 may be secured together by suitable means, e.g. epoxy, in order to assemble the spring housing assembly 28 to contain the needle 16 prior to engagement with the main housing 14.

In yet another filling and assembly procedure, the spring housing assembly 28 may initially be secured in engagement with the main housing 14. Then, the ampoule is positioned vertically with the open rear end of the barrel 14a facing upward to receive the medicinal fluid from a dispenser. If the surface tension of the fluid, and the diameter of the needle bore, are not sufficient to support the volume of dispensed fluid, then the tip of the needle 16 should be blocked or plugged to prevent the fluid from leaking out of the needle during filling. After the desired volume of fluid has been dispensed into the barrel 14a, the piston 18 is aligned with the rear of the barrel 14a and urged therein to the extent that a fluid seal is achieved between the piston 18 and the rear of the barrel 14a. The vertical orientation of the ampoule may then be reversed, so that the needle points upward. The tip of the needle 18 is then unplugged or unblocked. The piston 18 is then urged further into the barrel 14a to engage the tabs 45 with the annular detent 44. As the piston 18 is so positioned, any air within the barrel 14a will be purged from the ampoule through the needle 16. After the piston 18 has been properly positioned within the barrel 14a, the needle cap 19 is securely mounted onto the forward portion 14c of the housing 14 to subsequently shield the needle and to position the plug 24 upon the tip of the needle.

Other methods of filling the ampoule 10, such as by generating suction through the needle 16 by rearward motion of the piston 18, shall be apparent to those of skill in the art. Of course, an aseptic or antiseptic environment should be maintained throughout the filling procedure in order to maintain the desired purity of the medicinal fluid.

The barrel 14a of the ampoule 10, and the piston 18 therein, are preferably adapted for engagement with an injector assembly 12 of the type embodied in the "TUBEX" injector assembly, made by Wyeth-Ayerst Laboratories of Philadelphia, Pa. Briefly, the injector assembly 12 includes a body 71 having finger grips 74 extending therefrom. The injector assembly further includes a chuck 70 sized to receive the barrel 14a therein. The chuck 70 has a cylindrical collar 73 in threaded engagement with the body 71. After the barrel is inserted into the chuck 70, the collar 73 is screwed onto the body 71 in order to deform a concentric inner sleeve 72 of the chuck 70 into frictional engagement with the exterior of the barrel 14a. Alternatively, there may be employed an injector assembly such as that described in U.S. Pat. No. 4,642,103, the disclosure of which is incorporated by reference herein.

The injector assembly 12 further includes a plunger rod 76, which is slidably disposed within a central bore 77 formed in the body 71. A tip member 78 is attached to the forward end of the plunger rod 76. The tip member 78 has an axial bore for receiving the boss 58 of the piston 18, and is preferably internally threaded for securing engagement with the external threads formed on the boss 58. The rear end of the plunger rod 76 comprises a broadened actuating surface 76a upon which force is applied by a user during administration of an injection for urging the plunger rod 76 in the forward direction. The ampoule 10 is further compatible with other known injector assemblies, such as those wherein the ampoule 10 may be positioned as a cartridge within a cooperating channel of the injector assembly.

In order to administer the medicinal fluid to a patient, the injector assembly 12 is secured to the rear of the ampoule so that the chuck 70 grips the exterior of the barrel and the plunger rod tip 78 engages the boss 58. The cap 19 is then removed to expose the needle 16. The user may then administer the medicinal fluid to a patient by penetrating the skin of the patient and then urging the plunger rod 76 in the forward direction to cause the piston 18 to expel the medicinal fluid through the needle 16 and into the patient. Alternatively, the needle 16 may be used to penetrate an injection port of an intravenous access device connected with the patient, for administration of a so-called "IV push".

The barrel 14a is preferably transparent and has graduations (not shown) thereon for indicating the volume of fluid contained therein. Prior to administering the medicinal fluid to a patient, the user may expel an initial volume of fluid from the ampoule in order to obtain a desired, smaller dose of the fluid for delivery to the patient.

After the fluid has been administered to the patient, the needle 16 is removed from the patient, or from the injection port. The needle 16 may then be retracted into the ampoule 10 by the user applying a firm compressive force, preferably in excess of the force required to expel fluid during an injection stroke, to the rear of the plunger rod 76. A retraction mechanism responsive to such compressive force, which is described hereinbelow, then causes the needle 16 to be withdrawn in to the ampoule 10, so that the needle 16 no longer presents a sharp injury hazard. The injector assembly 12 is then removed from the ampoule 10, and the ampoule 10 may safely be discarded. It should be appreciated that the injector assembly 12 may subsequently be employed for connection with other ampoules of the same or similar type.

The retraction mechanism for effecting withdrawal of the needle comprises a latching mechanism 34 for selectively retaining the needle 16 in the projecting configuration. The latching mechanism 34 is formed to cooperate with the forward end of the piston 18 to release the needle 16 in response to a firm compressive force. The latching mechanism 34, and the cooperative structure of the piston 18, will now be described with continued reference to FIG. 1A.

The latch mechanism 34 preferably comprises a plurality of latching projections or fingers 36 formed at the rear end of the needle retaining member 32. The fingers 36 extend from the rearward portion of the needle retaining member into the conical portion 14b of the interior of the main housing 14. The barrel 14a extends rearwardly for the remainder of the length of the housing 14. The fingers 36 are provided with latches or hooks 38 integrally formed at the ends of the fingers 36. The hooks 38 extend radially inward for retaining the head 30 of the needle 16, so that the needle 16 is maintained in its projecting configuration for use. In the present preferred embodiment of the device, four fingers are employed, but more or less latching projections may be employed depending on the size of the device, the nature of any biasing member and related structure in the device for effecting optimum operation.

A spring 40 is compressed within the spring housing assembly 28 and surrounds the rear portion of the needle 16. In the configuration of FIG. 1A, the spring 40 is maintained in compression between the rear of the guideway 27 and the forward surface of the enlarged head 30 of the needle 16. An axial cavity or hollow area is provided in the needle retaining member 32 as well as in the front alignment member 26 which together define a spring housing chamber in which the needle and its surrounding spring are initially poised prior to use. The head 30 of the needle 16 functions as a cooperating latch member with the latching fingers 34. The needle head 30 provides an abutment for the rearward end of spring 40 for compressing the spring 40 against the rear of the guideway 27 within the interior of the front alignment portion 26. The needle head 30 forms a lip or rim that is maintained in abutment with the hooks 36 on the fingers 34. Hence, the needle 16 is held in a biased relationship which urges the needle toward the rear of the ampoule 10.

Figure 2:
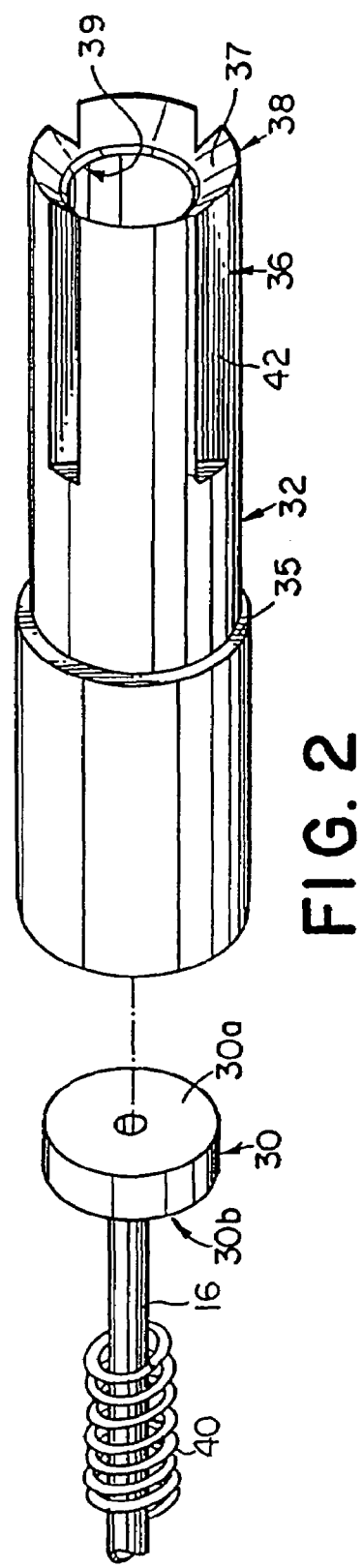
FIG. 2 is an exploded view of a latching assembly for selectively retaining the needle within the ampoule of FIG. 1A.

The cooperative relationships among the needle retaining member 32, needle head 30, needle 16, and the spring 40, are best shown in the exploded view of FIG. 2. As previously discussed, the needle retaining member 32 includes rearward extending fingers 36 or latching projections having hooks 38 formed at the terminal ends thereof. The fingers are preferably flexible to permit outward movement to release the cooperating latch abutment 30a provided by the head 30 of the needle 16. It should also be appreciated that the fingers 36 could be fractured when moved outwardly to release the needle head. The hooks 38 provide engaging surfaces 39 which extend radially inward for overlapping engagement with the abutment surface 30a of the head 30 of the needle 16.

The hooks 38 are formed to have rearward facing canted or wedge-shaped surfaces 37 for mating with the forward end of the piston 18, as described further hereinbelow. As should also be appreciated, should the fingers 36 be deformed or flexed radially outward, the engaging surfaces 38 of hooks 36 move out of abutment with the abutment surface 30a of the needle head 30. Upon this occurrence, the expansive force of spring 40 against the forward surface 30b of the needle head 30, immediately thrusts the needle head 30, and hence the needle 16, rearwardly toward the back or rear portion of the ampoule.

The latching projections or fingers 36 and the hooks 38 of the needle retaining member 32 are preferably joined together to form an annular latching member with a circular opening at the rear end. The retaining member 32 is provided with longitudinal grooves or score lines 42 running along the outside to facilitate breakage and separation of the fingers 36. The engaging surfaces 39 of the hooks 38 form a continuous rim within the interior of the needle retaining member 32, to enhance the security of engagement with the needle head 30. The continuous rim provides a seal with the rearward rim 30a of the needle head 30, so that fluid is kept out of the spring housing chamber. Additionally, a radially-protruding shoulder 35 is formed around the exterior of the needle retaining member 32 for abutment with a complementary ridge on the interior of the housing (not shown) to secure the needle retaining member 32 against being pushed rearward by the expansive force of the compressed spring 40.

Referring once again to FIG. 1A, the piston 18 comprises structural features for effecting release of the latching mechanism 34. The forward end of the axial cavity 48 is sealed by a frangible end member 52 formed centrally and integrally with the forward end of the piston 18. An annular joint 53 is thus formed between the frangible end member 52 and the remainder of the piston 18. The thickness of material forming the annular joint is sufficiently small such that the end member 52 can be broken or separated from the piston upon application of a force of less than about two pounds to the forward surface of the frangible end member. The latching mechanism 34 and the plunger 18 are preferably formed of a material that provides suitable frangibility for effecting needle retraction, while also being chemically compatible with the stored medication. Polystyrene, for example, provides such characteristics for use with various medications. The properties of frangibility and chemical compatibility may be provided separately by, for example, providing a conformal coating or layer of a chemically inert material, such as polytetrafluoroethylene, upon the surfaces of the plunger 18 and the latching mechanism 34 that are maintained in contact with the stored medication.

The periphery of the forward end of the piston 18 is contoured or tapered to mate with and abut the cooperating wedge shaped surfaces 37 of the hooks 36, for spreading the fingers 34 to release the hooks from the head of needle 16. More specifically, the piston 18 preferably has a tapered forward surface 50 which engages the complementary sloping faces 37 of the hooks, when the piston 18 is urged forward within the barrel 14a of the housing 14.

The forward progress of the piston 18 causes the fingers 34 to spread radially outward by flexing or breaking, thus releasing the head 30 of the needle 16. When the head 30 of the needle 16 is released, the needle 16 is thrust rearwardly by the spring 28 and is propelled by the spring force through the aperture formed in the forward end of the piston 18 by separation of the frangible end member 52 from the piston 18. The needle 16 is then received, and subsequently retained, within the cavity 48.

The ampoule 10 is shown in FIG. 1B with the injector assembly removed and the needle 16 in its retracted position within the cavity 48. When the needle is being retracted, and when the tip of the needle passes through aperture 27 into the spring housing assembly 28, the sealing member 29 relaxes, expanding from its formerly compressed condition to seal the forward end of the spring housing assembly 28 and to prevent any fluid from leaking out of the aperture 27.

In order to retain the piston 18 at the advanced position within the barrel 14 subsequent to needle retraction, the threaded tip of the plunger rod is preferably removed from the boss 58 prior to disengaging the injector chuck from the exterior of the barrel. Should the user remove the chuck from the barrel prior to disengaging plunger rod from the boss 58, then the piston 18 could be withdrawn within the barrel 14a as the injector assembly is removed. Provided that the piston 18 is not forcefully withdrawn, then the rearward motion of the piston 18 will be stopped by the detent 44. If the piston 18 is forcefully withdrawn during disengagement of the injector, then there is a possibility that the restraining influence of the detent 44 may be overcome, and thus piston 18 may be inadvertently removed from the rear of the barrel 14a. Preferably, then, the detent 44 and the tabs 45 are sufficiently firm to substantially prevent removal of the piston 18.

Other means may be provided to prevent removal of the piston 18 from the barrel 14a after retraction of the needle 16. For example, an additional, forward detent (not shown) may be formed within the interior of the barrel 14a for engaging the tabs 45 when the piston 18 is in the advanced position shown in FIG. 1B. Such an arrangement would be most suitable for embodiments in which the length of the injection stroke is less than or equal to the length of the piston, so that the forward detent would not disrupt the fluid seal between the piston 18 and the interior of the barrel 14a during the injection stroke. Alternatively, the engaging structure provided at the rear of the piston for mating with the tip of the plunger rod, may be arranged to permit the plunger rod to move the piston in only one direction. For example, the boss 58 may be provided without threads, yet having a sufficiently small diameter to fit within the tip of the plunger rod, for abutment with and alignment of the plunger rod. In such an abutting arrangement, forward movement of the plunger rod will urge the piston 18 in the forward direction within the barrel 14a, while any rearward movement of the plunger rod will merely cause the plunger rod and the boss 58 to dissociate from each other. Alternatively, the piston 18 can be structured to permit the boss 58, or a supporting portion of the piston 18, to dissociate from the remaining portion of the piston 18 if the plunger rod is withdrawn from the barrel 18.

As has been mentioned, retraction of the needle is effected by applying a forwardly directed force upon the piston in excess of the force required to eject fluid from the ampoule, yet comfortably within the normal range of strength of the user's hand. In order to ensure that the ampoule remains in secure engagement with the injector assembly, it may be desirable to configure the ampoule and the injector assembly to provide a positive, interlocking engagement therebetween, as an enhancement or alternative to the frictional engagement provided between the chuck 70 and the ampoule 10.

Referring now to FIG. 3, there is shown an ampoule 110 and an injector assembly 170 wherein means are provided for interlocking engagement of the injector assembly 170 with the ampoule 110. Similar parts in FIG. 3 to those shown in FIG. 1A are designated by the same reference number with the addition of 100 thereto. The ampoule 110 has a needle 116 extending from a spring housing assembly 128 that is secured within a main housing 114. The spring housing assembly 128 includes a latching mechanism (not shown) for selectively retaining the needle 116 in the projecting configuration and for releasing the needle 116 into cavity 148 in response to being actuated by the forward end of piston 118.

The barrel 114a of the ampoule 110 has a threaded portion 160 formed thereon. The injector assembly 112 has a sleeve or cup portion 170 extending from the body 171 of the injector assembly 112 for receiving the barrel 114a therein. A complementary threaded surface 172 is provided within the cup 170 for interlocking with the threaded surface 160 of the ampoule 110. A radially projecting surface, such as upon a flange 162, is provided upon the exterior of the barrel 114a to provide a stop for abutting against the forward peripheral surface 170a of the injector assembly 112, when the injector assembly is mounted upon the ampoule 110. The interlocking engagement of surfaces 160 and 172 of the respective ampoule 110 and injector assembly 112, provides enhanced security against inadvertently ejecting the ampoule 10 from the injector assembly 112 when retraction of the needle is desired.

Referring now to FIG. 4A, there is shown a self-contained pre-filled injection ampoule 210. The ampoule 210 is self-contained in the sense that a separate injector assembly is not required for operation of the ampoule 210. Rather, the function of a plunger rod, for pushing the piston 218, is provided by the needle cap 219, as described hereinbelow. Similar parts in FIG. 4 to those shown in FIG. 1A are designated by the same reference number with the addition of 100 thereto.

The ampoule 210 comprises a main housing 214, including a barrel 214a and a reduced diameter forward portion 214c. External projections, such as finger stops 274 are formed along the exterior of the barrel 214a. A volume of medicinal fluid 220 is contained within the barrel 214a. A piston 218 is slidably positioned within the rear of the barrel 214a. The rear portion 256 of the piston 218 is positioned in abutment with a detent 244 formed in the barrel 214a for preventing the piston 218 from being removed from the rear of the barrel. A spring housing assembly 228 is positioned within the forward portion 214c of the main housing 214 for selectively retaining a needle 216 in the projecting configuration. The forward portion of needle 216 is surrounded by a cap or sheath 219 that is removably attached to the exterior of the forward portion 214c of the housing 214. A plug member 224 is located or formed within the sheath 219 for receiving and sealing the tip of the needle 216.

The sheath 219 has piston engaging means, such as a receptacle member 278, formed on the forward end of the sheath 219. The receptacle member 278 is preferably threaded for engagement with a threaded boss 258 formed on the rear surface of the piston 218. When the ampoule 210 is to be employed for administering an injection, the sheath 219 is removed from the front of the ampoule 210 and is then mated to the rear of the piston 218 by engagement of the receptacle member 278 with the boss 258, as shown in FIG. 4B. An injection may then be given by depressing the rear portion 276 of the sheath 219 while applying a counteracting force to the finger stops 274, thus driving the piston 218 forward within the barrel 214a. A radially extending annular flange 273 is preferably formed upon the rear portion of the sheath 219 to provide a suitable surface for applying pressure to the rear of the sheath 219. In embodiments wherein the receptacle member 278 and the boss 258 are threaded, or otherwise interlocking, the sheath 219 may be withdrawn in order to draw fluid through the needle 216 and into the barrel 214a. Such withdrawal may be desirable, for example, to verify intravenous positioning of the tip of the needle 216, or to draw medicinal fluid into the barrel 214a for injection.

After an injection has been administered, the needle 216 is removed from the skin of the patient (not shown), or from the injection port of an intravenous fluid delivery system (not shown). Then, an additional compressive force may be applied to the rear portion 276 of the sheath 219 in order to effect retraction of the needle 216. The ampoule 210 is shown in FIG. 4C in the retracted configuration. In order to prevent withdrawal of the piston 218 after the needle has been retracted, stops or tabs 245 may be formed upon the exterior of the sheath for engaging detent 244 when the sheath 219 has been fully depressed into the barrel 214a.

As has been mentioned, it is desirable to store liquid medications in contact with materials that are compatible with such medications in terms of reactivity, solubility, impermeability, toxicity, etc. Because some medications should not be stored in contact with metal, such as with a needle, it is desirable to provide pre-filled injection ampoules in which the liquid medication is isolated from contact with the needle prior to use. One way to provide such isolation is by providing a puncturable membrane between the needle and the stored medication, and by providing a means for puncturing the membrane immediately prior to administering the desired injection.

Referring now to FIG. 5A, there is shown an injection ampoule 310, comprising a housing 314 that is formed to receive a sealed medication cartridge 304. The cartridge 304 is preferably made of an inert material, such as glass, for compatibility with a liquid medication 320 stored therein. The housing 314 and the cartridge 304 may be provided separately or in the assembled configuration shown in FIG. 5A. The forward end of the cartridge 304 is sealed by a puncturable membrane 301 which is preferably made of an elastomeric material. The membrane 301 is stretched to cover the front of the cartridge 304. The membrane 301 is held in position by an annular sealing ring 302 that is engaged within a circumferential exterior groove 305 formed about the forward end of the cartridge 304. The sealing member 302 may be an o-ring that is integrally formed with the membrane 301. Alternatively, the sealing member 302 may be a separate semi-rigid structure for compressively engaging the membrane with the forward end of the cartridge 304. A detent 306 is formed within the interior of the housing 314 for receiving the periphery of the sealing member 302 when in place about the forward end of the cartridge 304, and for retaining the cartridge within the housing 314 in the assembled configuration prior to use.

A piston 318 is positioned within the rear of the cartridge 304 in the initial configuration shown in FIG. 5A. The rear end of the cartridge 304 is open to provide access to the rear surface 356 of the piston 318 by a suitable plunger (not shown) for urging the piston in the forward direction within the cartridge 304 when an injection is administered. The rear surface 356 of the piston 318 may be provided with any of the several engagement or abutment means described hereinabove for mating with a piston. An axial cavity 348 is formed within the piston 318 for receiving the needle 316 when needle retraction is effected. An annular groove 323 is formed about the exterior of the forward end of the plunger for retaining a sealing member 322. The sealing member 322 includes an enlarged rim portion for engagement within the groove 323, and an attached puncturable membrane 322a preferably made of elastomeric material, that is stretched to cover the forward end of the piston 318. The membrane 322a also seals the forward end of the cavity 348.

A spring housing assembly 328 is positioned within the forward end of the main housing 314. The spring housing assembly releasably supports a needle 316 to extend from the forward end of the main housing 314 in the initial configuration.

Figure 6A:
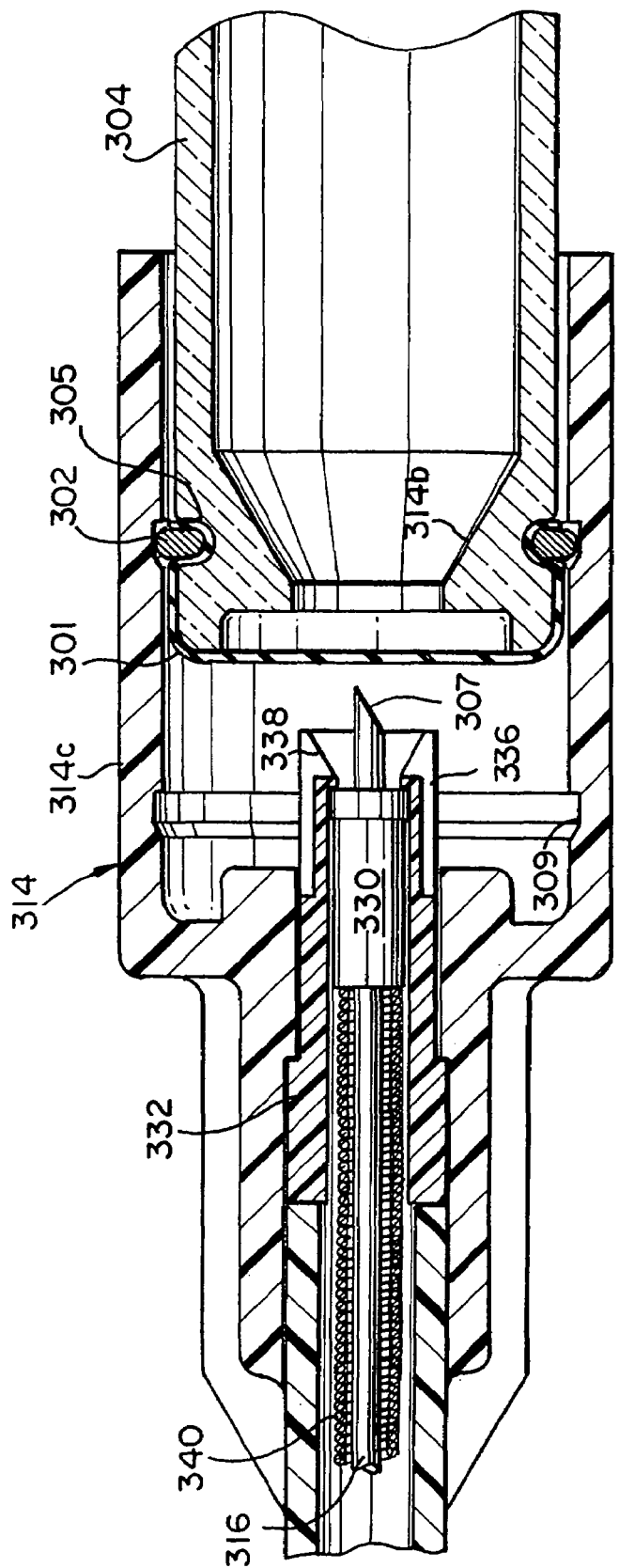
FIGS. 6A-6B are enlarged partial sectional views of portions of the injection ampoule shown in respective FIGS. 5A-5B.

Referring now to FIG. 6A, there is shown an enlarged view of a portion of the ampoule 310 with the cartridge 304 installed. An enlarged sleeve or head 330 surrounds the rear portion of the needle 316. The head 330 provides a cooperative latching assembly with the latching hooks 338 of the needle retaining member 332 in the manner described hereinabove. The needle 316 includes rear point 307 that extends rearwardly from the needle head 330 to a position within the main housing 314 beyond the rear end of the needle retaining member 332. In an alternative embodiment, the rearward facing needle point 307 may be provided as a separate needle member that is held in alignment with the forward facing needle 316 by the needle head 330.

Figure 6B:
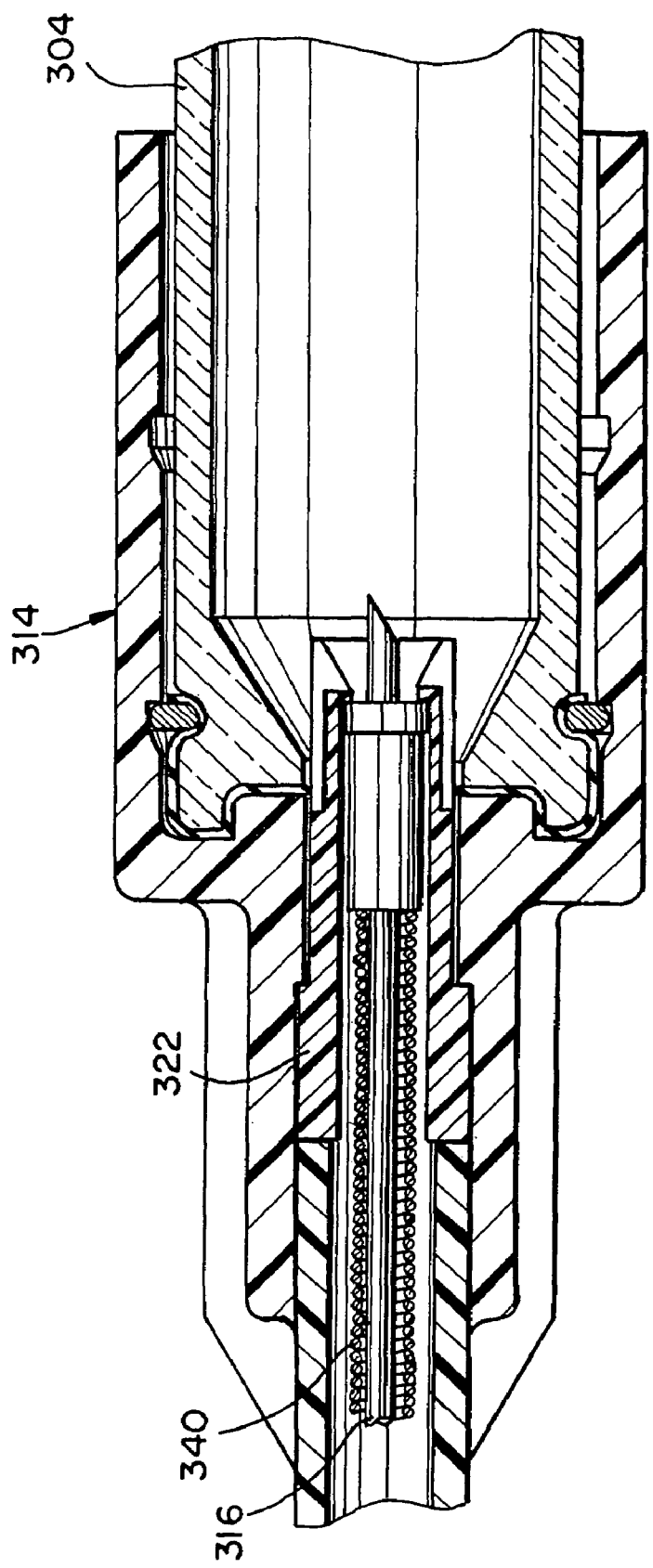

Before an injection is to be administered, the cartridge 304 is urged forward within the housing 314. As the cartridge 304 is urged forward, the membrane 301 is pierced by the rearward-facing needle point 307, and the neck 314b of the cartridge 304 is positioned to surround the fingers 336. When the cartridge 304 has been fully depressed into the housing 314, the sealing member 302 is engaged by detent 309, formed at a forward position within the housing 314, to retain the cartridge 304 within the housing 314 at the position shown in FIG. 6B. In alternative embodiments, the interior of the housing 314 and the forward end of the cartridge 304 may be provided with other engaging means, such as screw threads or bayonet slots, for retaining the cartridge 304 at the forward, or prepared, position. Such alternative engaging means may further comprise a locking mechanism for permanently retaining the cartridge 304 within the housing 314.

Referring now to FIG. 5B, the cartridge 304 is shown to be advanced within the housing 314 at the prepared position. The user may then attach a suitable injector assembly to the ampoule. For example, an injector assembly of the type described in connection with FIG. 1A may be secured to the rear of the cartridge 304. Alternatively, the injector assembly can be secured to the cartridge, and the plunger therein engaged with the piston 318, prior to advancing the cartridge 304 into the prepared position within the housing 314. In an alternative embodiment, a combined needle cap and plunger, such as has been described in connection with FIGS. 4A-C, may be engaged with the plunger 318 before or after the cartridge 304 is advanced to the prepared position. In yet another alternative embodiment, screw threads or other mating means may be formed on the exterior of the housing 314 for mating with an injector assembly such as that described in connection with FIG. 3. In such an embodiment, the injector assembly can be adapted to urge the cartridge into the prepared configuration as the injector assembly is mated to the housing 314.

Figure 5C:
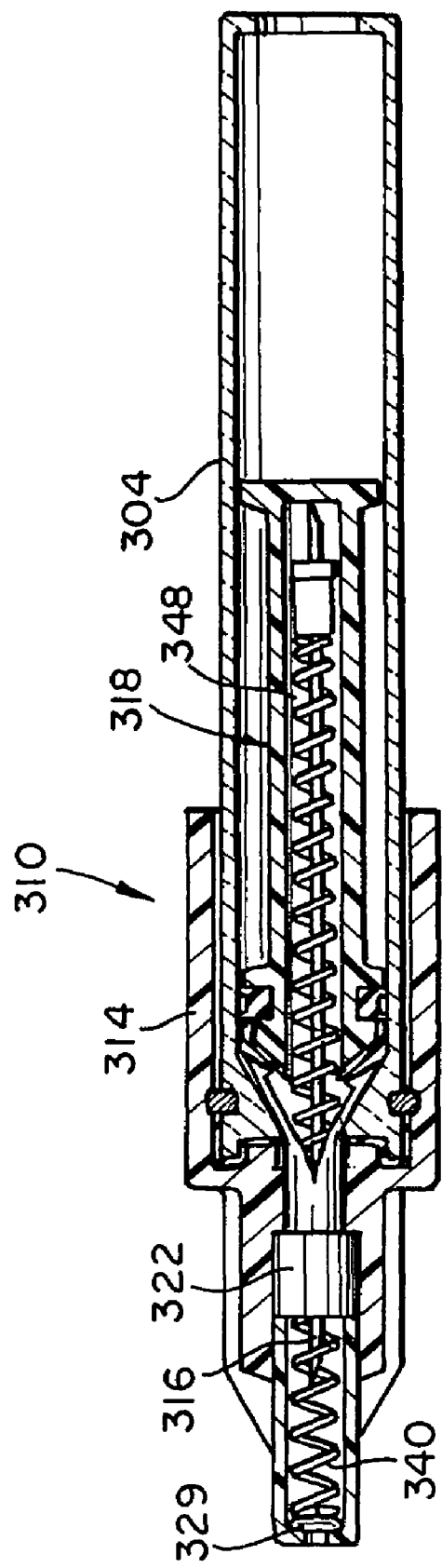
FIG. 5C is a partial sectional view of the injection ampoule of FIG. 5A, in a configuration after use thereof.

At the completion of an injection stroke, the piston 318 is sufficiently advanced within the cartridge 304 such that the membrane 322a sealing the forward end of the piston 318, will be ruptured by the piercing tip 307. A plunger stop or ridge (not shown) may be formed upon the interior surface of the cartridge 304 to provide a tactile signal to the user before the membrane 322a is ruptured. Upon feeling the tactile signal, the user may decide to preserve the integrity of the membrane 322a in order to subsequently aspirate additional fluid into the cartridge 304, or to effect needle retraction by further advancing the piston. In order to effect retraction, the user presses firmly upon the piston so that the piercing tip 307 ruptures the membrane 322a, and the fingers of the needle retaining member 332 are released by the forward end of the piston. The needle is then retracted into the plunger as shown in FIG. 5C.

In an alternative embodiment, other means for piercing the cartridge membrane 301 may be provided. For example, the rear end of one or more of the hooks 338 of the needle retraction member 332 may be sharpened or provided with a rearward facing point in order to puncture the membrane 301. In such an embodiment, the rearward-facing needle point 307 may be eliminated. Additionally, the plunger 318 may be of the type having an integrally-formed frangible end as described hereinabove, rather than having a sealing membrane 322a.

Figure 7A:
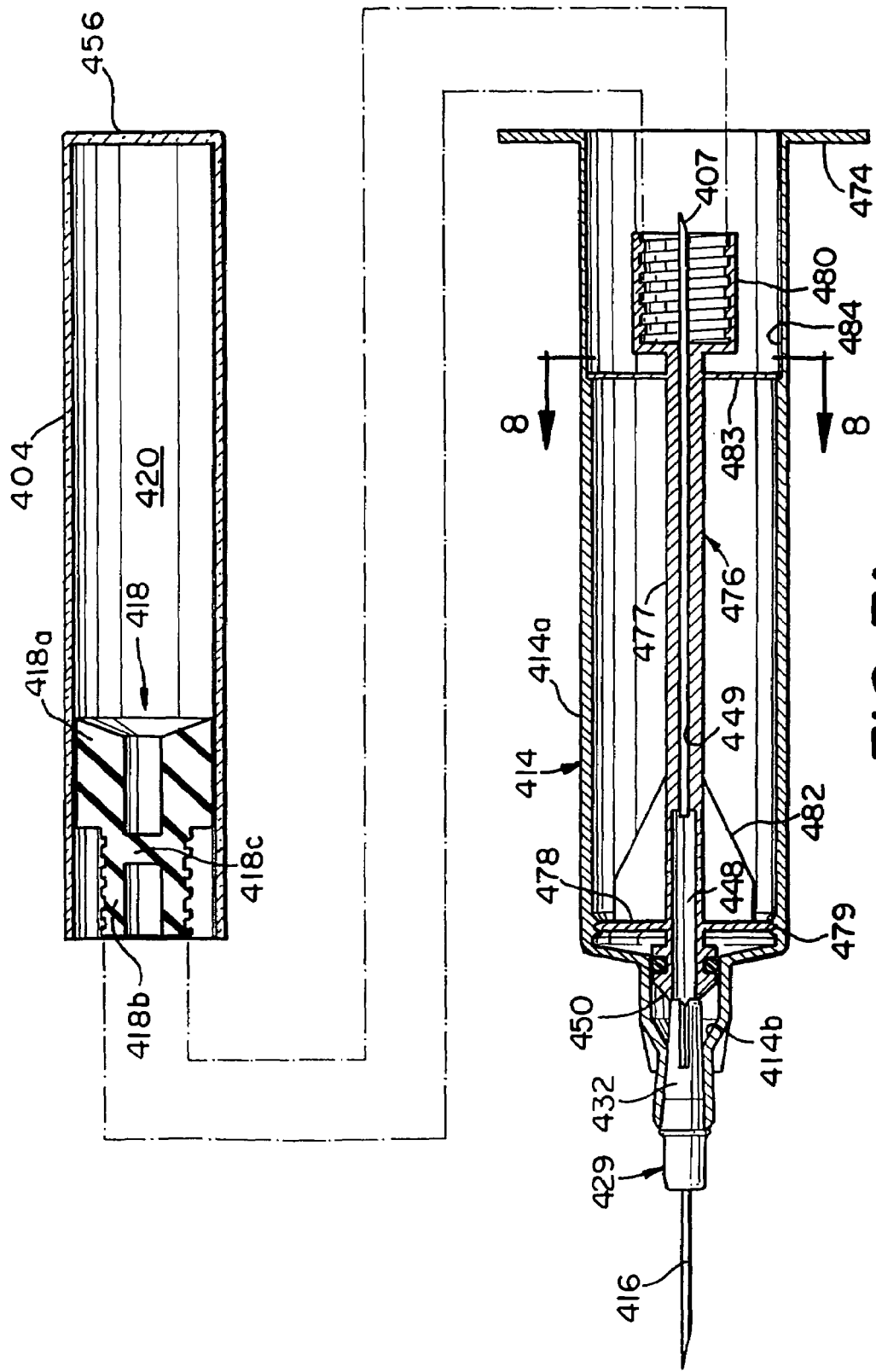

Referring now to FIG. 7A, there is shown another embodiment of a retractable-needle unit dose injection device. In the device shown in FIG. 7A, a stationary plunger 476 is provided for holding a piston 418 in a fixed position as a pre-filled cartridge 404 is urged into the main housing 414 of the device. The cartridge 404 is of a known type having a slidable elastomeric piston 418 within the forward end of the cartridge 404 for sealing a volume of liquid medication 420 in the cartridge 404. The piston 418 includes an enlarged diameter rear portion 418a forming a slidable fluid seal with the interior of the cartridge 404, and a reduced diameter forward portion 418b. The rear portion 418a and the forward portion 418b of the piston each have respective axially-aligned bores formed therein. A puncturable septum 418c is formed within the piston 418 between the axial bores within the respective front and rear portions of the piston 418. The exterior surface of the forward portion 418b is threaded or otherwise adapted for mating with the stationary plunger 476, as described hereinbelow.

The injection device comprises a main housing 414 having a spring housing 429 installed therein for releasably holding a needle 416 in a projecting configuration from the forward end of the main housing 414. The spring housing 429 includes a needle retaining member 432, which extends rearwardly into a neck portion 414b of the housing 414. The neck portion 414b of the housing 414 opens into an enlarged barrel portion 414a of the housing 414. The stationary plunger 476 comprises a rod 477 that is centrally positioned within housing 414. The positioning of the plunger 476 is maintained by a radial member, such as by radial struts or a seating disk 478. The rim of the disk 478 is held within a groove 479 formed about the interior of the barrel 414a.

An actuating head 450 is formed on the forward end of the rod 477 for actuating the needle retaining member 432. The actuating head 450 extends into the neck 414b of the housing, and is positioned behind the needle retaining member 432. A needle-receiving bore 448 is formed within the head 450 and extends into the rod 477 for a sufficient length to receive the rear of the needle when retraction of the needle is effected. The rear end of the bore 448 joins with a reduced diameter fluid channel 449 that extends rearwardly for the remainder of the length of the rod 477.

A cup or receptacle 480 is formed at the rear end of the rod 477. The cup 480 is sized to receive the forward portion 418b of the piston 418 therein. Suitable mating surfaces, such as screw threads, are formed within the cup 480 for secure engagement with the piston 418. A rearward-facing hollow needle 407 is joined with the channel 449 and is centrally aligned within the cup 480. When the piston 418 is mated with the plunger 476, the needle 407 pierces the septum 418c to provide a fluid passageway from the interior of the cartridge 404 to the forward needle 416.

In embodiments wherein the mating means between the piston 418 and the plunger 476 comprises screw threads, it is desirable to provide the plunger 476 with structure for resisting torsional stress or rotation as the piston and plunger are joined. Several such features may be employed. For example, radial stiffening ribs 482 may be formed upon the exterior of the rod 477 and joined to the seating disk 478. The head 450 of the plunger 476 and the neck 414b of the housing 414 may have a non-circular or polygonal perimeter so as to resist rotation of the plunger 476 when the cartridge 404 is installed.

Figure 8:
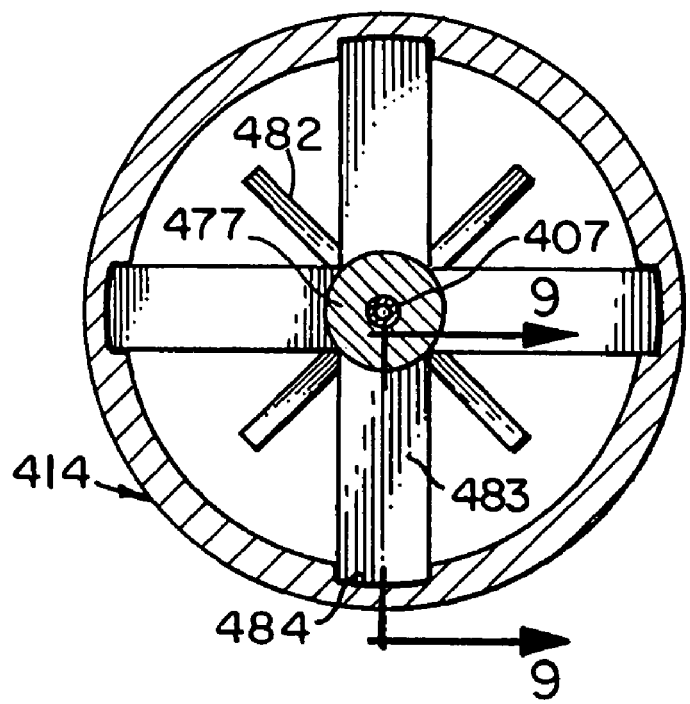
FIG. 8 is a sectional view of the injection ampoule taken along the line 8-8 of FIG. 7A.
Figure 9:
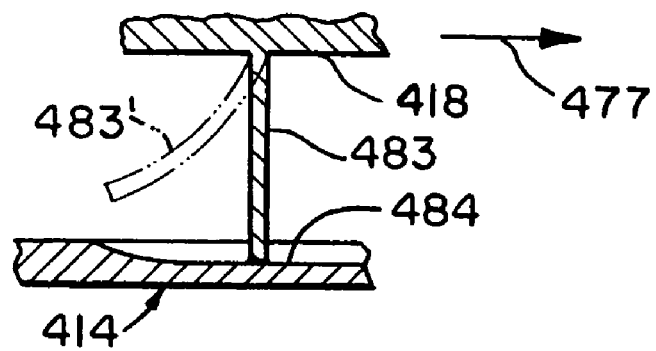
FIG. 9 is a sectional view of a portion of an injection ampoule taken along the line 9-9 of FIG. 8.

Another torsion resistant structure includes radial struts 483 that are joined to the rod 477 and extend into recesses 484 formed in the interior of the barrel 414a. The struts 483 are preferably located toward the rear of the rod 477 and adjacent to the forward end of the cup 480. The struts 438 are configured to flex in the forward direction to permit the cartridge 404 to pass between the rod 477 and the interior of the barrel 414a as an injection is given. Accordingly, the struts 483 are thin enough to permit such flexing in the forward direction. The struts 483 are also broad enough, as shown in FIG. 8 to resist lateral, or circumferential, flexing. Additionally, as shown in FIG. 9, the recesses 484 extend in the forward direction along the interior of the barrel beyond the point of engagement with the struts 483 to permit the struts 483 to flex into the configuration designated 483' during use.

After the piston 418 has been engaged with the plunger 476, an injection may be given by the user applying a compressive force between the finger stops and the rear surface 456 of the cartridge 404. At the completion of an injection stroke, as shown in FIG. 7B, the forward end of the cartridge 404 abuts the seating disk 478. In order to effect retraction of the needle 416, the user may then apply firm pressure to the rear surface 456 of the cartridge 404, which force is then transmitted by the cartridge 404 to the seating disk 478 in order to drive the rim of the seating disk 478 out of engagement with the recess 479. When the seating disk 478 is disengaged from the recess 479, the plunger 476 is urged forward within the housing 414 so that the actuating head 450 unlatches the needle retaining member 432. As shown in FIG. 7C, the needle 416 is then retracted into the cavity 448. In the preferred embodiment, the housing 414 is sized to receive the entire length of the cartridge 404 therein so that subsequent withdrawal of the cartridge 404 from the housing 414 is prevented.

Figure 10:
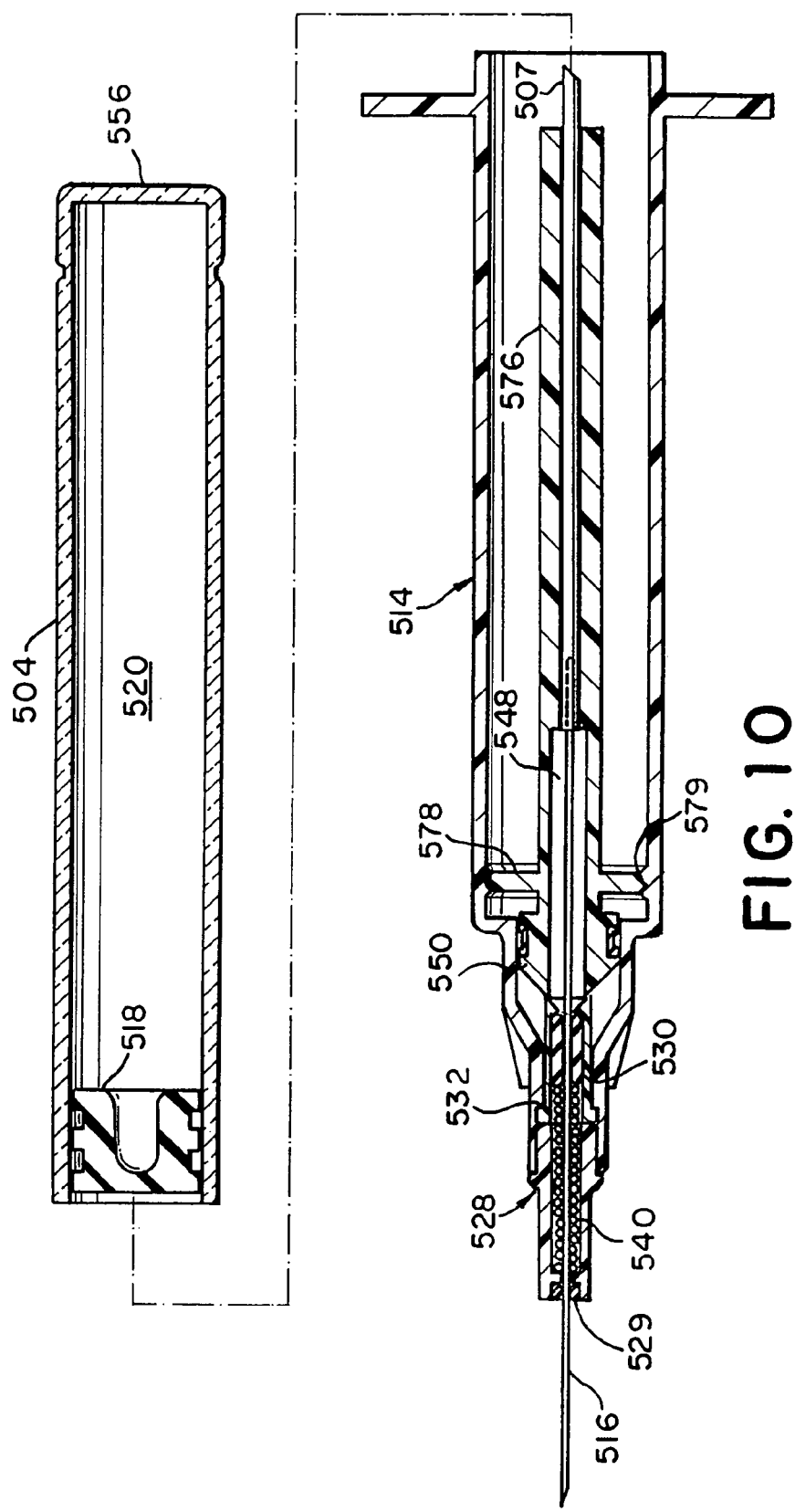
FIG. 10 is a sectional view of a sixth embodiment of a retractable needle injection ampoule apparatus.

Referring now to FIG. 10, there is shown another embodiment of a retractable needle unit dose injection device. In the device shown in FIG. 10, a stationary plunger 576 is provided for holding a piston 518 in a fixed position as a pre-filled cartridge 504 is urged into the main housing 514 of the device. A retaining skirt or flange 578 is formed about the plunger 576 for securing the plunger 576 within the housing 514. The rim of the flange 578 is held within annular detents 579 formed on the interior surface of the housing wall 514. When the cartridge 504 is urged into the rear opening of housing 514, the piston 518, which initially serves as a stopper for the cartridge 504, is pierced by a rearward facing piercing needle 507 that is axially positioned to extend from the rear of the plunger 576.

An injection needle 516 is telescopically positioned within at least a portion, the forward portion, of the rearward facing piercing needle 507. The injection needle 516 extends from within the forward end of the piercing needle 507, through the forward end 550 of the plunger 576 into spring housing 528, and out of the forward end of the spring housing 528 in an extended configuration. The injection needle 516 is selectively held in the extended configuration by retaining member 532. An enlarged sleeve or collar 530 is affixed about a central portion of the needle 516 to provide a rim or lip for the fingers of the retaining member 532 to retain the needle 516 against the rearward bias exerted thereon by spring 540, in a manner similar to the retaining arrangements previously described.

After an injection has been administered, retraction of the needle 516 is effected by the user pushing against the rear surface 556 of the cartridge 504 so that the forward end of the cartridge 504 will, in turn, urge retaining flange 578 out of engagement with detent 579. Consequently, the plunger 576, and particularly the head 550 formed thereon, will be driven against the fingers of retaining member 532, and needle 516 will be released in the manner described hereinabove in connection with other embodiments of the invention. When the needle 516 is released from the retaining member 532, expansion of spring 540 will drive the collar 530, and the attached needle 516, rearwardly within an axial cavity 548 formed in the forward end of the plunger 576. The rear portion of needle 516 will thus be telescopically received further within the forward portion of piercing needle 507. The forward end of needle 516 will thus be received and subsequently retained within the device.

As should be appreciated, needle 516 is sized to have an outer diameter that is less than the inner diameter of piercing needle 507, in order to facilitate telescopic positioning of injection needle 516 within the piercing needle 507. The initial axial extent of the telescopic positioning, and the radial clearance provided between the two needles, are selected to substantially prevent fluid leakage into the cavity 548 while an injection is given. These dimensional tolerances allow substantially all of the fluid initially contained within cartridge 504 to be injected into a patient, with minimal retention of fluid within the injection device after an injection is given. In order to substantially prevent any fluid that may be retained within the piercing needle 507 or the injection needle 516 from leaking out of the device after retraction of the piercing needle 507 has been effected, an expanding seal member 529 is provided within the spring housing 528. The seal member 529 initially surrounds the needle 516 and is compressed within an annular groove formed at the forward end of the spring housing 528. When the point of the injection needle 516 is retracted into the spring housing 528, the seal member 529 is permitted to expand to seal the forward end of the device.

The terms and expressions which have been employed are used as terms of description and not of limitation. There is no intention in the use of such terms and expressions of excluding any equivalents of the features shown and described or portions thereof. It is recognized, however, that various modifications are possible within the scope of the invention as claimed.

That which is claimed is:

1. A method for providing an injection from a medical device, comprising the steps of:
   providing a medical device comprising a barrel, a retractable needle, a mounting stem having a connector that is cooperable with a cartridge containing a quantity of medicinal fluid, wherein the mounting stem is spaced apart from the barrel to provide an annular passage, the mounting stem extending longitudinally within the barrel along a majority of a length of the barrel, and the device comprises a radial member connected with the mounting stem and releasably engaging a recess in the barrel to retain the stem in a fixed axial position relative to the barrel during an injection;
   providing a cartridge containing a quantity of medicinal fluid, comprising a fluid container and a seal comprising a connector cooperable with the connector on the stem;
   attaching the cartridge to the mounting stem by connecting the seal connector with the stem connector;
   displacing the fluid container forwardly through the annular passage until the fluid container engages the radial member, whereby while the fluid container is displaced forwardly the stem maintains the seal in a fixed axial position, relative to the barrel;
   displacing the fluid container further forwardly after the fluid container engages the radial member so that the fluid container displaces the radial member, disengaging the radial member from the recess and effecting release of the needle; and
   retracting the needle after release via a biasing element biasing the needle rearwardly.

2. The method of claim 1 comprising the step of piercing the seal to provide fluid communication between the fluid container and the needle.

3. The method of claim 1 wherein the fluid container comprises a fluid chamber having a length and extending from the rearward end of the seal to the rearward end of the container, and wherein the step of displacing the fluid container comprises displacing the fluid container forwardly a distance that is substantially similar to the length of the fluid chamber.

4. The method of claim 1 wherein the medical device comprises a second radial member disposed in a proximal portion of the barrel, the second radial member retaining the stem in a fixed axial position relative to the barrel.

5. A method for providing an injection from a medical device, comprising the steps of:
   providing a medical device comprising a barrel, a needle having a sharpened tip projecting forwardly from the barrel, a biasing element biasing the needle rearwardly, and a mounting stem disposed within the barrel;
   releasably retaining the mounting stem in a fixed axial position relative to the barrel by a radial member attached to the mounting stem and engaging a recess in the barrel;
   providing a cartridge comprising a fluid container containing a quantity of medicinal fluid and a slidable seal forming a fluid-tight seal with the container;
   attaching the seal to the stem to connect the cartridge to the medical device;
   retaining the seal in a fixed axial position relative to the barrel while displacing the fluid container forwardly over the seal to expel the fluid from the container and through the needle; and
   displacing the fluid container further forwardly after the fluid container engages the radial member, thereby disengaging the radial member from the recess and causing the needle to be released for retraction.

6. The method of claim 5 comprising the step of retracting the needle so that the sharpened tip of the needle is retracted into the barrel.

7. The method of claim 5 comprising the step of piercing the seal to provide fluid communication between the fluid container and the needle.

8. The method of claim 5 wherein the fluid container comprises a fluid chamber having a length that extends from the rearward end of the seal to the rearward end of the container, and wherein the step of retaining the seal while displacing the fluid container comprises displacing the fluid container forwardly a distance that is substantially similar to the length of the fluid chamber.

9. A medical device for providing an injection of fluid, comprising:
- a hollow housing having a central axis;
- an ampoule of fluid comprising a container having a length, an open end forming a rim and a plug sealing the open end, wherein the container comprises a fluid chamber having a length that extends from a rearward end of the plug to the rearward end of the container;
- a needle having a sharpened tip operable between a projecting position in which the sharpened tip projects forwardly from the housing and a retracted position in which the sharpened tip is shielded against inadvertent contact;
- a biasing element biasing the needle toward the retracted position;
- a stem disposed within the housing configured to matingly engage the ampoule plug to attach the plug to the stem wherein the stem is operable in connection with the ampoule to provide an injection of fluid through the needle from the ampoule by displacing the ampoule forwardly relative to the stem;
- a first radial member disposed in a distal portion of the housing, the first radial member releasably retaining the stem at a fixed axial position during the injection wherein when the ampoule is mounted on the stem, the first radial member is spaced from the rim of the container a distance substantially similar to the length of the fluid chamber so that at the end of the injection the ampoule engages the first radial member; and
- a second radial member disposed in a proximal portion of the housing, the second radial member maintaining the stem aligned parallel with the axis of the housing;
- wherein after the ampoule engages the first radial member, continued forward displacement of the ampoule operates to effectuate release of the needle.

10. The medical device of claim 9 wherein the plug has a piercable wall for providing access to the medicine in the ampoule.

11. The medical device of claim 10 comprising a piercing element projecting from the stem that is operable to pierce the wall of the plug.

12. The medical device of claim 11 wherein the piercing element is in fluid communication with the sharpened tip.

13. The medical device of claim 9 wherein the housing comprises a recess cooperable with the first radial member.

14. The medical device of claim 9 comprising a needle retainer releasably retaining the needle in the extended position against the bias of the spring.

15. The medical device of claim 9 wherein the container comprises a closed end forming a manually operable surface for displacing the container relative to the housing.

16. The medical device of claim 9 wherein the rearward end of the housing is open, forming a socket for receiving the ampoule.

17. The medical device of claim 9 wherein the second radial member is configured to flex to permit the container to pass between the stem and the hollow housing during forward displacement of the ampoule.

* * * * *